(12) United States Patent
Ishikawa et al.

(10) Patent No.: US 9,101,761 B2
(45) Date of Patent: Aug. 11, 2015

(54) MOVING OBJECT TRACKING SYSTEM FOR RADIOTHERAPY

(75) Inventors: Masayori Ishikawa, Sapporo (JP); Naoki Miyamoto, Sapporo (JP); Tsuyoshi Sasagawa, Kyoto (JP); Seiji Yamanaka, Kyoto (JP); Junichi Yamazaki, Mukou (JP); Masayuki Yamaji, Hirakata (JP); Hirokazu Yamawaki, Takatsuki (JP)

(73) Assignees: NATIONAL UNIVERSITY CORPORATION HOKKAIDO UNIVERSITY, Hokkaido (JP); SHIMADZU CORPORATION, Kyoto (JP)

( * ) Notice: Subject to any disclaimer, the term of this patent is extended or adjusted under 35 U.S.C. 154(b) by 151 days.

(21) Appl. No.: 14/006,658

(22) PCT Filed: Mar. 21, 2012

(86) PCT No.: PCT/JP2012/001959
§ 371 (c)(1),
(2), (4) Date: Sep. 20, 2013

(87) PCT Pub. No.: WO2012/127865
PCT Pub. Date: Sep. 27, 2012

(65) Prior Publication Data
US 2014/0018604 A1 Jan. 16, 2014

(30) Foreign Application Priority Data
Mar. 22, 2011 (JP) .................................. 2011-062631

(51) Int. Cl.
*H05G 1/02* (2006.01)
*A61N 5/10* (2006.01)
*A61B 6/00* (2006.01)

(52) U.S. Cl.
CPC ............ *A61N 5/1048* (2013.01); *A61B 6/4452* (2013.01); *A61B 6/487* (2013.01); *A61N 5/1049* (2013.01); *A61N 2005/1061* (2013.01)

(58) Field of Classification Search
CPC .......... H05G 1/02; A61B 6/44; A61B 6/4429; A61B 6/4435; A61B 6/4452; A61B 6/4464; A61B 6/487
USPC ........................................... 378/42, 193, 197
See application file for complete search history.

(56) References Cited

U.S. PATENT DOCUMENTS 6,307,914 B1   10/2001   Kunieda et al.

FOREIGN PATENT DOCUMENTS

| JP | 63-290548 A | 11/1988 |
| JP | 3053389 B1 | 6/2000 |
| JP | 2008-544833 A | 12/2008 |

OTHER PUBLICATIONS

International Search Report issued in PCT/JP2012/001959 dated May 22, 2012 with English Translation.
TM-M132031B "Mistsubishi Electron Tube Supporting Structure RT-STAND Instruction Manual" Mitsubishi Electric Corp., Nov. 2002 and its partial English Translation (front page, p. 1-1 and 2-5).

*Primary Examiner* — Jurie Yun
(74) *Attorney, Agent, or Firm* — McDermott Will & Emery LLP (57) ABSTRACT

In the case where X-ray tubes and X-ray detectors have fixed directions (directions of irradiation and directions of detecting planes), X-ray fluoroscopy can be carried out from various directions by providing two U-shaped tracks for the X-ray tubes and the X-ray detectors, each having two straight tracks arranged opposite each other, and a curved track connected thereto. An increased number of directions for X-ray fluoroscopy can be secured by arranging a U-shaped track rail for the X-ray tubes and a U-shaped track rail for the X-ray detectors opposite each other when seen in plane view.

2 Claims, 7 Drawing Sheets

MOVING OBJECT TRACKING SYSTEM FOR RADIOTHERAPY

RELATED APPLICATIONS

This application is the U.S. National Phase under 35 U.S.C. 371 of International Application No. PCT/JP2012/001959, filed on Mar. 21, 2012, which in turn claims the benefit of Japanese Application No. 2011-062631, filed on Mar. 22, 2011, the disclosure of which Applications are incorporated by reference herein.

TECHNICAL FIELD

This invention relates to a moving object tracking system for radiotherapy which tracks a moving body concerning a treatment part by X-ray fluoroscopy in order to irradiate the treatment part with radiation.

BACKGROUND ART

Conventionally, stereotactic radiotherapy of the head has been developed first, which is directed to the head maintained still, and stereotactic radiotherapy of the trunk portion has been developed next, which carries out radiotherapy for the whole body in a state of the trunk portion fixed, by regarding a tumor of a treatment part as not movable either. However, when radiotherapy is carried out for the whole body in a state of the trunk portion fixed, the patient will be subjected to bodily pain and mental anguish. Besides, even if the trunk portion is fixed, the tumor of the treatment part is not necessarily in a fixed position without actually moving.

So, stereotactic radiotherapy has been developed in recent years, which carries out radiotherapy by placing a marker on a body surface of the patient, tracking the marker placed on the body surface using respiratory synchronization of the patient, and irradiating the treatment part with radiation when it comes to a predetermined position by respiration (e.g. expiratory cycles). However, the movement of the marker placed on the body surface and the movement of the tumor in the body are not necessarily in agreement.

So, a moving object tracking system for radiotherapy has been developed in recent years, which tracks also a tumor of a treatment part by embedding a marker near the tumor in the body, and tracking the marker by X-ray fluoroscopy. This moving object tracking system for radiotherapy carries out radiotherapy by irradiating the treatment part with radiation when the marker comes to a predetermined position (see Patent Document 1, for example).

The conventional moving object tracking system for radiotherapy has imaging systems as X-ray fluoroscopy for tracking the moving object, and the imaging systems includes X-ray tubes for emitting X-rays, and X-ray detectors (for example, X-ray detectors of the image intensifier or flat panel type) for detecting the X-rays. With the conventional stationary type moving object tracking system for radiotherapy, the imaging systems are fixedly arranged on a ceiling and a floor. Of the imaging systems, the X-ray tubes are arranged on the floor and the X-ray detectors are arranged on the ceiling, for example. Since the direction and position of X-ray fluoroscopy are fixed in this stationary type, two or more sets (e.g. four sets) of imaging systems are needed in order to carry out X-ray fluoroscopy from various directions.

In order to reduce the number of sets of imaging systems, the imaging systems are placed and moved on circular movable seats. Or each of the X-ray tubes and the X-ray detectors is moved along an arcuate track (e.g. arcuate rail) (see Nonpatent Document 1, for example). In this way, instead of the stationary type, the imaging systems including the X-ray tubes and X-ray detectors may be moved, thereby to reduce the number of sets of imaging systems and realize X-ray fluoroscopy from various directions.

In order to avoid a complicated drive system for driving the imaging systems, the X-ray tubes have fixed directions of irradiation, and the X-ray detectors have detecting planes with fixed directions. Therefore, as in Nonpatent Document 1 noted above, wherever on the arcuate tracks as shown in a plane view of FIG. 8, the X-ray tubes T have fixed directions of irradiation toward a tumor center (which is considered "isocenter" of treatment), and the X-ray detectors D have detecting planes with fixed directions for detecting transmitted X-rays from the isocenter, such being an arrangement of each. Therefore, even if their directions are fixed, the X-ray tubes T and X-ray detectors D are moved along the arcuate tracks, respectively, to be able to carry out X-ray fluoroscopy from various directions on the arcuate tracks.

PRIOR ART DOCUMENTS

Patent Document

[Patent Document 1]
U.S. Pat. No. 3,053,389

Nonpatent Document

[Nonpatent Document 1]
TM-M132031B "Mitsubishi Electron Tube Supporting Structure RT-STAND Instruction Manual" Mitsubishi Electric Corp., November 2002

DISCLOSURE OF THE INVENTION

Problem to be Solved by the Invention

However, the imaging systems having fixed directions on tracks other than the arcuate tracks cannot carry out X-ray fluoroscopy from various directions. Straight tracks R as shown in a side view of FIG. 9, for example, are not curved tracks like the arcuate tracks, and therefore the direction of X-ray fluoroscopy (X-ray tubes T and X-ray detectors D) will be always constant. Thus, when the direction is fixed, the main problems are that the number of sets of imaging systems should be reduced, and that X-ray fluoroscopy should desirably be carried out from various directions.

Figure 8:
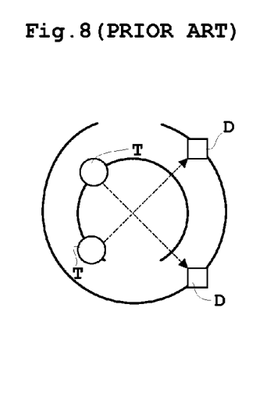
FIG. 8 is a plane view schematically showing X-ray tubes and X-ray detectors arranged on conventional arcuate tracks.

On the other hand, since the directions of the imaging systems are fixed, whichever positions they may be on the arcuate tracks as shown in the plane view of FIG. 8 as in Nonpatent Document 1 noted above, there is a problem that X-ray fluoroscopy can by carried out only adjacent the isocenter. Usually, when tracking a moving object, a gold marker formed of gold may be embedded as a tracking target, but there can be a case where the gold marker cannot be embedded near a tumor. As a specific example, a gold marker is indwelled in the bronchus with a bronchial endoscope when treating lung cancer. The place for indwelling is a bronchus end, for example, in which case it is practically impossible to do the indwelling. In such a case, the gold marker indwelled in a place distant from the isocenter will be tracked by X-ray fluoroscopy, and it is desired to enlarge the range of X-ray fluoroscopy in order to track the moving object also in positions other than the isocenter.

Figure 9:
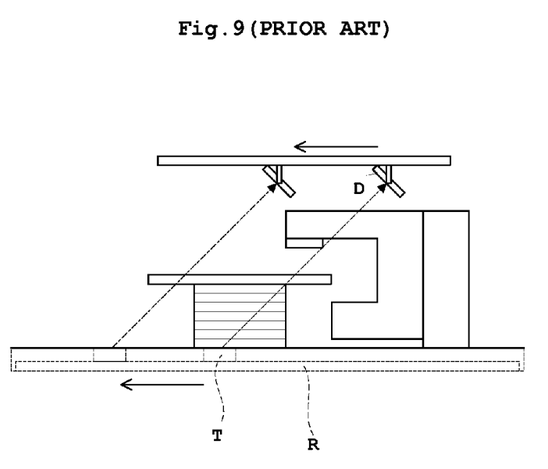
FIG. 9 is a side view schematically showing X-ray tubes and X-ray detectors arranged on conventional straight tracks.

On tracks other than the arcuate tracks, and on the straight tracks R as shown in the side view of FIG. 9 noted above, the direction of X-ray fluoroscopy is always constant. However, X-ray fluoroscopy can be carried out from various positions by moving along the straight tracks to positions easy to carry out X-ray fluoroscopy. Therefore, the range of X-ray fluoroscopy can be enlarged in order to track the moving object also in positions other than the isocenter. So, when the direction is fixed on tracks other than the straight tracks, there are also problems that the number of sets of imaging systems should be reduced, and that X-ray fluoroscopy should desirably be carried out from various positions to enlarge the range of X-ray fluoroscopy.

This invention has been made having regard to the state of the art noted above, and its object is to provide a moving object tracking system for radiotherapy which can carry out X-ray fluoroscopy from various directions when the directions of an X-ray tube and an X-ray detecting device are fixed.

Means for Solving the Problem

To fulfill the above object, this invention provides the following construction.

A moving object tracking system according to this invention is a moving object tracking system for radiotherapy for tracking a moving object concerning a treatment part by X-ray fluoroscopy in order to irradiate the treatment part with radiation, comprising an X-ray tube having a fixed direction of X-ray irradiation for the X-ray fluoroscopy; an X-ray detecting device with a detecting plane having a fixed direction for detecting X-rays emitted from the X-ray tube to carry out the X-ray fluoroscopy; and two U-shaped tracks for the X-ray tube and the X-ray detecting device, each having two straight tracks arranged opposite each other, and a curved track connected thereto; wherein the U-shaped track for the X-ray tube and the U-shaped track for the X-ray detecting device are arranged opposite each other when seen in plane view.

[Functions and Effects] With the moving object tracking system for radiotherapy according to this invention, by providing two U-shaped tracks for the X-ray tube and X-ray detecting device, each consisting of two straight tracks arranged opposite each other and a curved track connected thereto, X-ray fluoroscopy can be carried out from various direction, as distinct from the simply straight tracks R as shown in the side view of FIG. 9. Compared with the arrangement as shown in the plane view of FIG. 5 in which the U-shaped track for the X-ray tube and the U-shaped track for the X-ray detecting device are arranged in the same direction instead of being arranged opposite each other when seen in plane view, an arrangement as shown in the plane view of FIG. 3 or 4 in which the U-shaped track for the X-ray tube and the U-shaped track for the X-ray detecting device are arranged opposite each other can secure an increased number of directions for X-ray fluoroscopy. As a result, the main problem that the number of sets of the imaging systems consisting of the X-ray tube and X-ray detecting device should be reduced, and X-ray fluoroscopy desirably is carried out from various directions, can be solved, and X-ray fluoroscopy can be carried out from various directions when the X-ray tube and X-ray detecting device have fixed directions (direction of irradiation and direction of the detecting plane).

In the above invention, it is preferred to comprise a control device for controlling the X-ray tube and the X-ray detecting device to move in the same direction along the straight tracks of the U-shaped track for the X-ray tube and the U-shaped track of the X-ray detecting device, respectively. As on the simply straight tracks R as shown in the side view of FIG. 9, on the respective straight tracks of the U-shaped track for the X-ray tube and the U-shaped track for the X-ray detecting device as shown in the plane view of FIG. 6, the X-ray tube and X-ray detecting device can be moved in the same direction along these tracks. Therefore, movement can be made along these tracks to positions easy to carry out X-ray fluoroscopy. As a result, in addition to the above main problem, a problem that the number of sets of the imaging systems consisting of the X-ray tube and X-ray detecting device should be reduced, and X-ray fluoroscopy desirably is carried out from various positions to enlarge the range of X-ray fluoroscopy, can also be solved, when the X-ray tube and X-ray detecting device have fixed directions (direction of irradiation and direction of the detecting plane) on tracks other than the simply straight tracks R as shown in the side view of FIG. 9.

Effects of the Invention

The moving object tracking system for radiotherapy according to this invention provides two U-shaped tracks for the X-ray tube and X-ray detecting device, each consisting of two straight tracks arranged opposite each other and a curved track connected thereto. The U-shaped track for the X-ray tube and the U-shaped track for the X-ray detecting device are arranged opposite each other when seen in plane view, whereby X-ray fluoroscopy can be carried out from various directions when the X-ray tube and X-ray detecting device have fixed directions (direction of irradiation and direction of the detecting plane).

BRIEF DESCRIPTION OF THE DRAWINGS

FIGS. 3(*a*)-(*e*) are plane views of one example schematically showing respective U-shaped tracks arranged opposite each other;

FIGS. 4(*a*)-(*e*) are plane views of an example different from FIG. 3, schematically showing respective U-shaped tracks arranged opposite each other;

FIGS. 5(*a*)-(*c*) are plane views used for comparison with FIG. 3 and FIG. 4, and schematically showing respective U-shaped tracks arranged in the same direction instead of opposite each other;

FIGS. 6(*a*)-(*d*) are plane views schematically showing X-ray tubes and X-ray detectors moved in the same direction along straight tracks of respective U-shaped tracks;

EMBODIMENTS

Embodiments of this invention will be described hereinafter with reference to the drawings.

Figure 1:
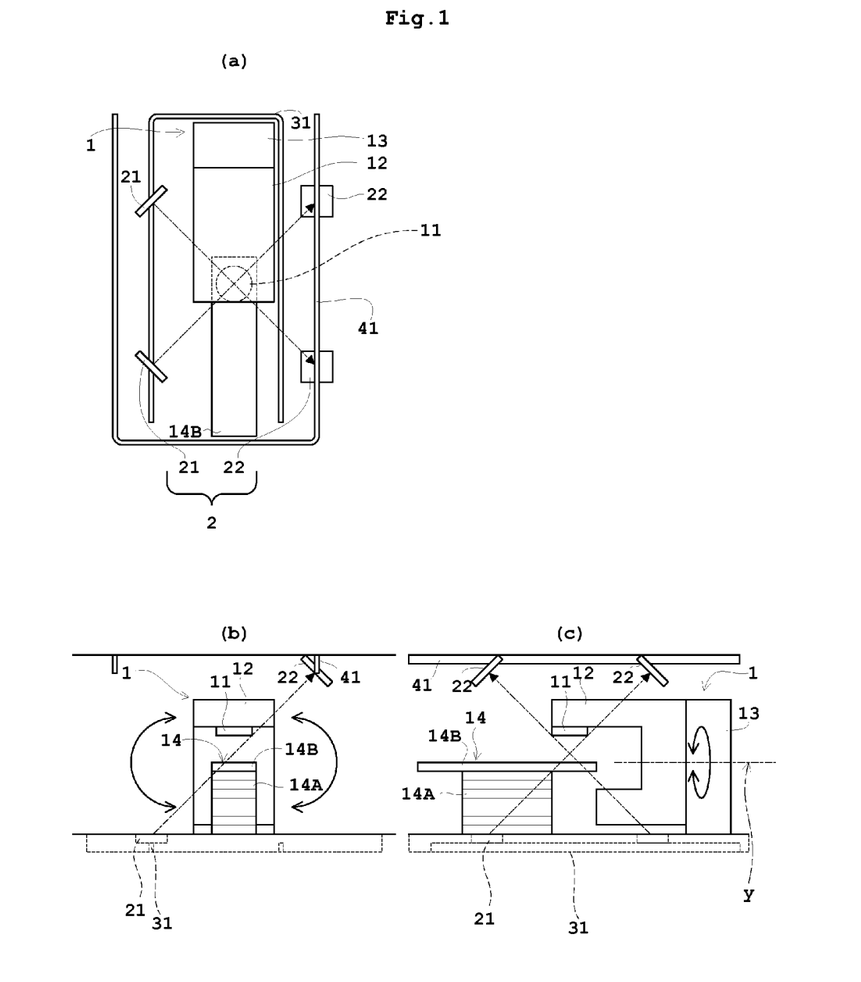
FIG. 1 is a schematic view of a moving object tracking system for radiotherapy according to an embodiment, in which (*a*) is a plane view, (*b*) is a front view, and (*c*) is a right side view.
Figure 2:
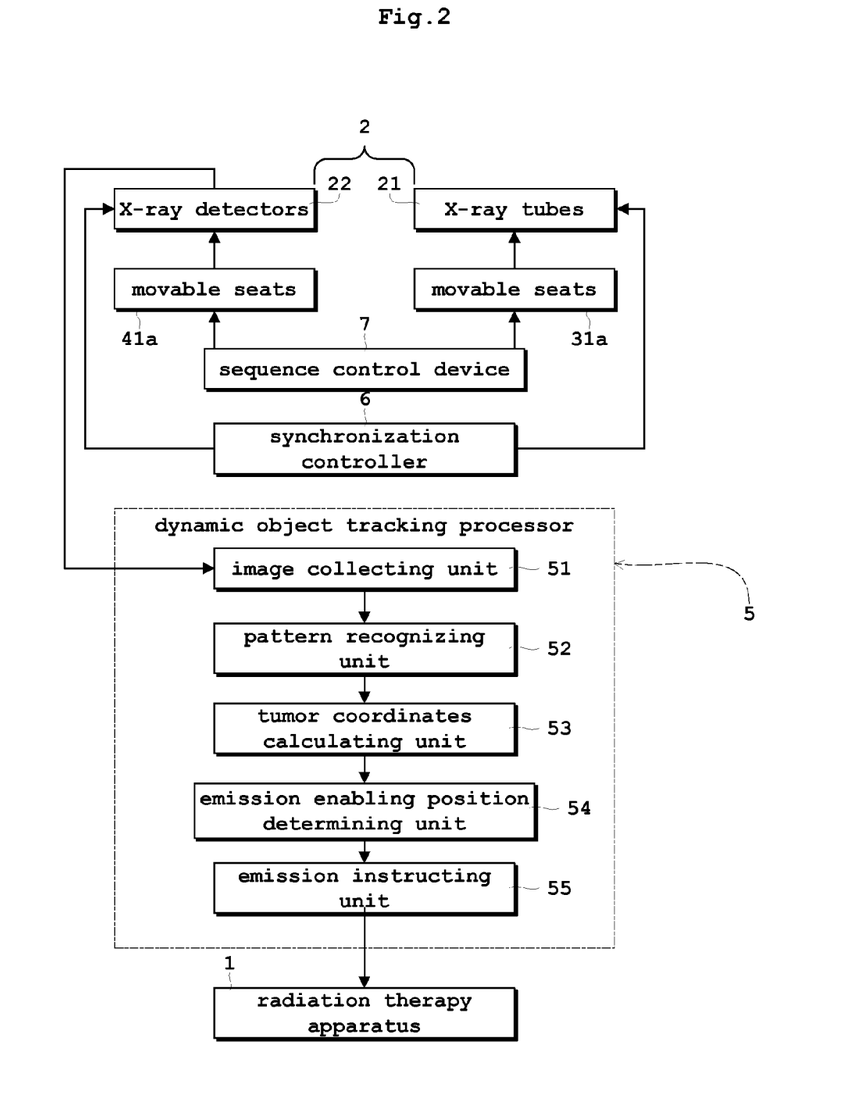
FIG. 2 is a block diagram of the moving object tracking system for radiotherapy according to the embodiment.

FIG. 1 is a schematic view of a moving object tracking system for radiotherapy according to an embodiment. FIG. 2 is a block diagram of the moving object tracking system for radiotherapy according to the embodiment.

As shown in FIG. 1, the moving object tracking system for radiotherapy includes imaging systems 2 (see the plane view of FIG. 1(a)), and is used in combination with a radiation therapy equipment 1. The radiation therapy equipment 1 is the linear accelerator type called liniac or linac, or the particle beam equipment type such as of proton beam or carbon beam, and includes a radiation source 11 which emits X-rays, particle beams or the like to a treatment part, a gantry 12 which has the radiation source 11 mounted inside and is rotatable in directions shown in FIG. 1(b) about y-axis shown in FIG. 1(c), a base block 13 which supports the gantry 12 and is disposed on a floor or a wall surface, and a bed 14 on which a patient (not shown) is placed to be treated. The bed 14 includes a lift deck 14A which can move up and down vertically, and a top board 14B on which the patient is placed and which is horizontally slidable relative to the lift deck 14A.

As shown in the plane view of FIG. 1(a), the imaging systems 2 include X-ray tubes 21 which emit X-rays for X-ray fluoroscopy, and X-ray detectors 22 which detect the X-rays for X-ray fluoroscopy. As shown in FIG. 1, the X-ray tubes 21 emit X-rays toward a tumor center which corresponds to an isocenter of treatment, and the X-ray detectors 22 detect X-rays transmitted through the isocenter. The X-ray detectors 22 are not limited to a particular type, as long as they are in ordinary use as exemplified by image intensifier or flat panel type X-ray detectors. The X-ray tubes 21 correspond to the X-ray tube in this invention. The X-ray detectors 22 correspond to the X-ray detecting device in this invention.

In FIG. 1, the imaging systems 2 (see the plane view of FIG. 1(a)) are provided in two sets. Specifically, two X-ray tubes 21 are provided, and so are two X-ray detectors 22. There is no limitation to the number of sets of imaging systems 2.

Figure 3:
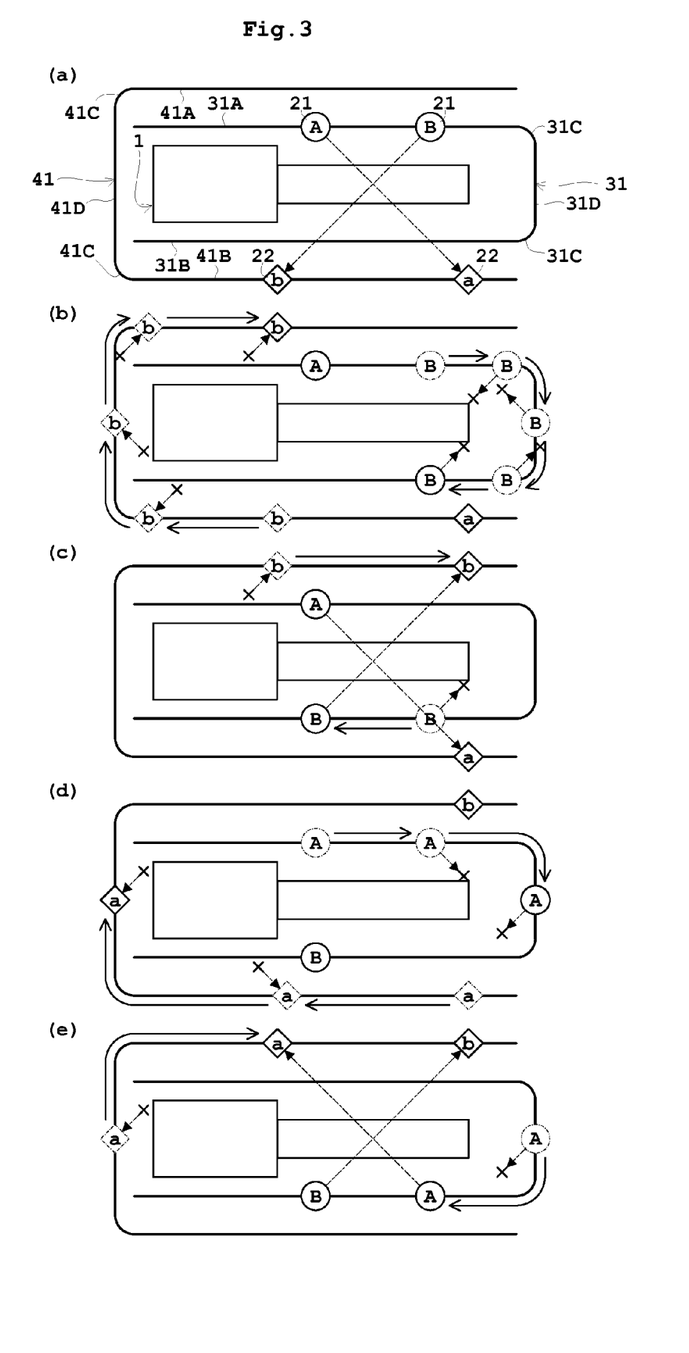
Figure 4:
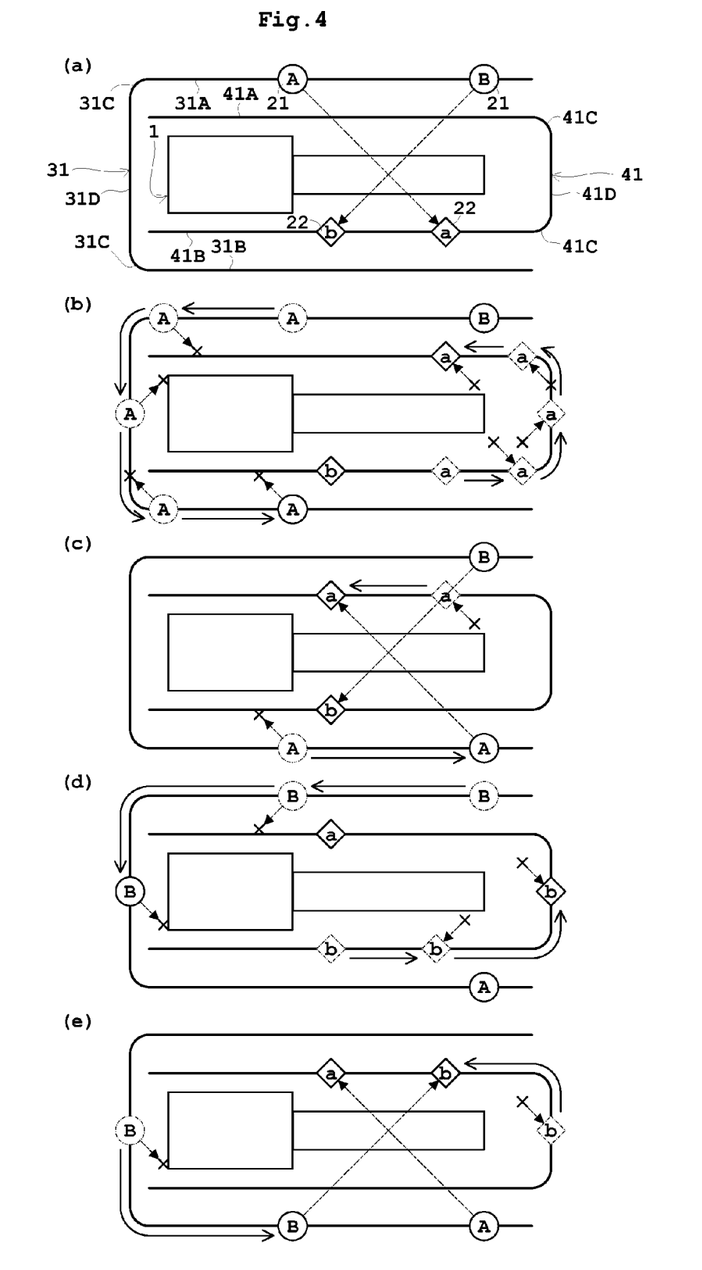
Figure 6:
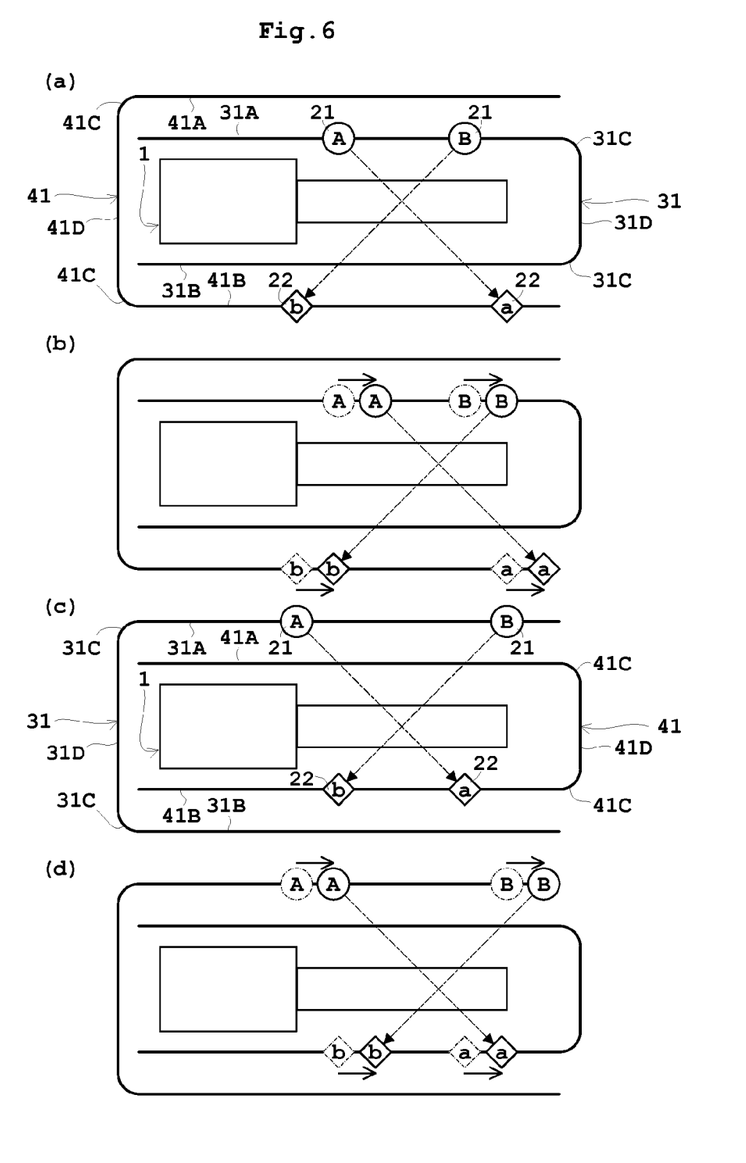

The X-ray tubes 21 have fixed directions of irradiation, and the X-ray detectors 22 have detecting planes with fixed directions. With the directions fixed in this way, as shown in FIGS. 3, 4 and 6 described hereinafter, the X-ray tubes 21 emit X-rays in the directions shown in each figure, and the X-ray detectors 22 detect the X-rays in the directions shown in each figure.

In addition, the moving object tracking system for radiotherapy has a rail 31 for the X-ray tubes 21 which is laid as embedded under the floor. The X-ray tubes 21 are moved along the rail 31. The rail 31 is a U-shaped track which, as shown in FIGS. 3, 4 and 6 described hereinafter, includes two straight tracks 31A and 31B arranged opposite each other, and curved tracks 31C connected thereto. The moving object tracking system for radiotherapy also has a rail 41 for the X-ray detectors 22 laid on a ceiling surface. The X-ray detectors 22 are moved along the rail 41. The rail 41 is a U-shaped track which, as shown in FIGS. 3, 4 and 6 described hereinafter, includes two straight tracks 41A and 41B arranged opposite each other, and curved tracks 41C connected thereto. For expediency of illustration, FIG. 1 and FIGS. 3, 4 and 6 described hereinafter show only single rails, but it may be a construction for moving the imaging systems 2 (see the plane view of FIG. 1(a)) consisting of the X-ray tubes 21 and X-ray detectors 22 along two or more rails. The rail 31 for the X-ray tubes 21 corresponds to the U-shaped track for the X-ray tube. The rail 41 for the X-ray detectors 22 corresponds to the U-shaped track for the detecting device.

As shown in the plane view of FIG. 1(a), the rail 31 which is the U-shaped track for the X-ray tubes 21 and the rail 41 which is the U-shaped track for the X-ray detectors 22 are arranged opposite each other when seen in plane view. In FIG. 1(a), the rail 31 for the X-ray tubes 21 is shown inward and the rail 41 for the X-ray detectors 22 outward, but this is not limitative. As shown in FIG. 4 described hereinafter, the rail 31 for the X-ray tubes 21 may be located outward, and the rail 41 for the X-ray detectors 22 inward. Since the rail 31 is disposed under the floor and the rail 41 is disposed on the ceiling surface, the respective rails 31 and 41 may be arranged to overlap vertically when seen in plane view.

In addition, as shown in FIG. 2, the moving object tracking system for radiotherapy includes a moving object tracking processor 5 for processing moving object tracking. The moving object tracking processor 5 has an image collecting unit 51, a pattern recognizing unit 52, a tumor coordinates calculating unit 53, an emission enabling position determining unit 54, and an emission instructing unit 55.

In addition, as shown in FIG. 2, the moving object tracking system for radiotherapy includes a synchronization controller 6 and a sequence control device 7 for controlling the imaging systems 2. The above moving object tracking processor 5, synchronization controller 6 and sequence control device 7 are constructed of a central processing unit (CPU) and the like. The synchronization controller 6 controls the X-ray tubes 21 and X-ray detectors 22 of the imaging systems 2 to operate synchronously with one another. The sequence control device 7 controls the X-ray tubes 21 and X-ray detectors 22, through movable seats 31a which move the X-ray tubes 21 and movable seats 41a which move the X-ray detectors 22, to move along the respective straight tracks 31A and 41A (see FIGS. 3, 4 and 6) of the rail 31 (see FIG. 1) for the X-ray tubes 21 and the rail 41 (see.

FIG. 1) for the X-ray detectors 22 synchronously in the same directions. The sequence control device 7 can also control the X-ray tubes 21 and X-ray detectors 22 to move along the respective straight tracks 31B and 41B (see FIGS. 3, 4 and 6) of the rails 31 and 41 synchronously in the same directions. The sequence control device 7 corresponds to the control device in this invention.

The image collecting unit 51 of the moving object tracking processor 5 collects X-ray images obtained by X-ray fluoroscopy based on the X-rays emitted from the X-ray tubes 21 and detected by the X-ray detectors 22 of the imaging systems 2. The pattern recognizing unit 52 of the moving object tracking processor 5 carries out matching of image information of a marker obtained beforehand and target X-ray images, and carries out pattern recognition as to whether the marker is reflected in the target X-ray images based on results of the matching. The tumor coordinates calculating unit 53 of the moving object tracking processor 5 derives coordinates of the tumor by calculation based on a positional relationship between the embedded marker and the tumor. The emission enabling position determining unit 54 of the moving object tracking processor 5 determines emission enabling positions from whether the coordinates of the tumor are in a predetermined position (e.g. position of expiratory cycles). The emission instructing unit 55 of the moving object tracking processor 5 inputs an enabling signal to the radiation therapy equipment 1 for permitting emission of the radiation from the radiation source 11 (see FIG. 1) of the radiation therapy equipment 1 when the coordinates of the tumor come to the predetermined position (e.g. position of expiratory cycles).

Figure 5:
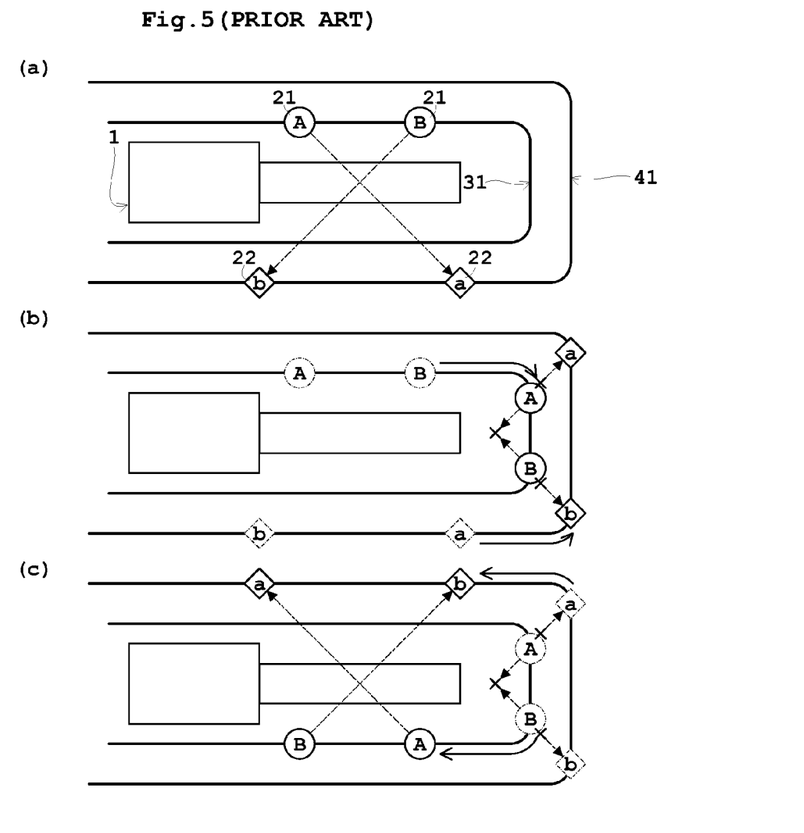

Next, specific arrangements of the rails will be described with reference to FIGS. 3 and 4, and a conventional arrangement of rails will be described with reference to FIG. 5 for comparison with FIGS. 3 and 4. FIG. 3 presents plane views of one example schematically showing respective U-shaped tracks arranged opposite each other. FIG. 4 presents plane views of an example different from FIG. 3, schematically showing respective U-shaped tracks arranged opposite each other. FIG. 5 presents plane views used for comparison with FIG. 3 and FIG. 4, and schematically showing respective U-shaped tracks arranged in the same direction instead of opposite each other.

FIGS. 3-5 are plane views of the time when the imaging systems 2 are provided in two sets (see the plane view of FIG. 1 (*a*), or FIG. 2). In FIGS. 3-5, the X-ray tubes 21 of the imaging systems 2 are depicted in circles representing the shape of tube balls, and the X-ray detectors 22 of the imaging systems 2 are depicted in squares representing the shape of flat panel type X-ray detectors. Of the two sets of imaging systems 2, the X-ray tube 21 of one imaging system 2 is indicated with capital letter "A", the X-ray detector 22 of the same imaging system 2 is indicated with small letter "a", the X-ray tube 21 of the other imaging system 2 is indicated with capital letter "B", and the X-ray detector 22 of the same imaging system 2 is indicated with small letter "b". FIGS. 3-5 indicate with "x" when the directions of irradiation of the X-ray tubes 21 and the detecting planes of the X-ray detectors 22 do not face each other.

As shown in FIG. 3(*a*), FIG. 4(*a*), and FIG. 6 described hereinafter, the rail 31 for the X-ray tubes 21 is a U-shaped track consisting of two straight tracks 31A and 31B arranged opposite each other, curved tracks 31C connected thereto, and a straight track 31D connected to the tracks 31C. As shown in FIG. 3(*a*), FIG. 4(*a*), and FIG. 6 described hereinafter, the rail 41 for the X-ray detectors 22 is a U-shaped track consisting of two straight tracks 41A and 41B arranged opposite each other, curved tracks 41C connected thereto, and a straight track 41D connected to the tracks 41C. As shown in FIG. 3, FIG. 4, and FIG. 6 described hereinafter, the rail 31 for the X-ray tubes 21 and the rail 41 for the X-ray detectors 22 are arranged opposite each other when seen in plane view.

FIG. 3 will be described first. As shown in FIG. 3, the rail 31 for the X-ray tubes 21 describes a U-shaped track extending around the front of the radiation therapy equipment 1 (see FIG. 3 (*a*)), and the rail 41 for the X-ray detectors 22 describes a U-shaped track extending around the back of the radiation therapy equipment 1. In FIG. 3, the rail 31 for the X-ray tubes 21 is located inward, and the rail 41 for the X-ray detectors 22 outward. As noted hereinbefore, the rail 31 for the X-ray tubes 21 may be located outward, and the rail 41 for the X-ray detectors 22 inward. Since the rail 31 is disposed under the floor and the rail 41 is disposed on the ceiling surface, the respective rails 31 and 41 may be arranged to overlap vertically when seen in plane view.

As shown in FIG. 3(*a*), with each having a fixed direction, an arrangement is made such that X-rays emitted from the X-ray tube 21 of one imaging system 2 (see the plane view of FIG. 1(*a*), or FIG. 2) are detected by the X-ray detector 22 of the same imaging system 2 (see "A" and "a" of FIG. 3(*a*)). Similarly, an arrangement is made such that X-rays emitted from the X-ray tube 21 of the other imaging system 2 are detected by the X-ray detector 22 of the same imaging system 2 (see "B" and "b" of FIG. 3(*a*)).

When, with the X-ray tube 21 and X-ray detector 22 of one imaging system 2 (see the plane view of FIG. 1(*a*), or FIG. 2) fixed, the X-ray tube 21 and X-ray detector 22 of the other imaging system 2 are moved along the rails 31 and 41 (see FIG. 3(*a*)), respectively, in the direction of arrows in FIG. 3(*b*), the direction of irradiation of the X-ray tube 21 and the detecting plane of the X-ray detector 22 do not face each other in each movement zone. When the X-ray tube 21 and X-ray detector 22 are further moved, respectively, the X-ray detector 22 detects X-rays emitted from the X-ray tube 21 in the position shown in FIG. 3(*c*).

Now, when, with the X-ray tube 21 and X-ray detector 22 of the other imaging system 2 (see the plane view of FIG. 1(*a*), or FIG. 2) fixed, the X-ray tube 21 and X-ray tube 22 of the one imaging system 2 are moved along the rails 31 and 41 (see FIG. 3 (*a*)), respectively, in the direction of arrows in FIG. 3(*d*), the direction of irradiation of the X-ray tube 21 and the detecting plane of the X-ray detector 22 do not face each other in each movement zone. When the X-ray tube 21 and X-ray detector 22 are further moved, respectively, the X-ray detector 22 detects X-rays emitted from the X-ray tube 21 in the position shown in FIG. 3(*e*).

Thus, the X-ray tubes 21 having fixed directions of irradiation and the X-ray detectors 22 having fixed directions of detecting planes, and when, as shown in FIG. 3, the imaging systems 2 (see the plane view of FIG. 1(*a*), or FIG. 2) are provided in two sets, realize a combination of directions of X-ray fluoroscopy shown in FIG. 3(*a*), a combination of directions of X-ray fluoroscopy shown in FIG. 3(*c*), and a combination of directions of X-ray fluoroscopy shown in FIG. 3(*e*). Therefore, a total of three combinations are realized, excluding the case of moving the X-ray tubes 21 and X-ray detectors 22 in the same direction as shown in FIG. 6 described hereinafter.

FIG. 4 will be described next. As shown in FIG. 4, the rail 31 for the X-ray tubes 21 describes a U-shaped track extending around the back of the radiation therapy equipment 1 (see FIG. 4(*a*)), and the rail 41 for the X-ray detectors 22 describes a U-shaped track extending around the front of the radiation therapy equipment 1. In FIG. 4, the rail 31 for the X-ray tubes 21 is located outward, and the rail 41 for the X-ray detectors 22 inward. Also in the case of FIG. 4 in which the rail 31 for the X-ray tubes 21 describes a U-shaped track extending around the back of the radiation therapy equipment 1, and the rail 41 for the X-ray detectors 22 describes a U-shaped track extending around the front of the radiation therapy equipment 1, the rail 31 for the X-ray tubes 21 may be located inward, and the rail 41 for the X-ray detectors 22 outward. Since the rail 31 is disposed under the floor and the rail 41 is disposed on the ceiling surface, the respective rails 31 and 41 may be arranged to overlap vertically when seen in plane view.

As shown in FIG. 4(*a*), with each having a fixed direction, an arrangement is made such that X-rays emitted from the X-ray tube 21 of one imaging system 2 (see the plane view of FIG. 1(*a*), or FIG. 2) are detected by the X-ray detector 22 of the same imaging system 2 (see "B" and "b" of FIG. 4(*a*)). Similarly, an arrangement is made such that X-rays emitted from the X-ray tube 21 of the other imaging system 2 are detected by the X-ray detector 22 of the same imaging system 2 (see "A" and "a" of FIG. 4(*a*)).

When, with the X-ray tube 21 and X-ray detector 22 of one imaging system 2 (see the plane view of FIG. 1(*a*), or FIG. 2) fixed, the X-ray tube 21 and X-ray detector 22 of the other imaging system 2 are moved along the rails 31 and 41 (see FIG. 4(*a*)), respectively, in the direction of arrows in FIG. 4(*b*), the direction of irradiation of the X-ray tube 21 and the detecting plane of the X-ray detector 22 do not face each other in each movement zone.

When the X-ray tube 21 and X-ray detector 22 are further moved, respectively, the X-ray detector 22 detects X-rays emitted from the X-ray tube 21 in the position shown in FIG. 4(*c*).

Now, when, with the X-ray tube 21 and X-ray detector 22 of the other imaging system 2 (see the plane view of FIG. 1(*a*), or FIG. 2) fixed, the X-ray tube 21 and X-ray tube 22 of the one imaging system 2 are moved along the rails 31 and 41 (see FIG. 4 (*a*)), respectively, in the direction of arrows in FIG. 4(*d*), the direction of irradiation of the X-ray tube 21 and the detecting plane of the X-ray detector 22 do not face each other in each movement zone. When the X-ray tube 21 and X-ray detector 22 are further moved, respectively, the X-ray detector 22 detects X-rays emitted from the X-ray tube 21 in the position shown in FIG. 4(e).

Thus, the X-ray tubes 21 having fixed directions of irradiation and the X-ray detectors 22 having fixed directions of detecting planes, and when, as shown in FIG. 4, the imaging systems 2 (see the plane view of FIG. 1(a), or FIG. 2) are provided in two sets, realize a combination of directions of X-ray fluoroscopy shown in FIG. 4(a), a combination of directions of X-ray fluoroscopy shown in FIG. 4(c), and a combination of directions of X-ray fluoroscopy shown in FIG. 4(e). Therefore, a total of three combinations are realized, excluding the case of moving the X-ray tubes 21 and X-ray detectors 22 in the same direction as shown in FIG. 6 described hereinafter.

As described above, in the case where the rail 31 for the X-ray tubes 21 and the rail 41 for the X-ray detectors 22 are arranged opposite each other when seen in plane view as shown in FIG. 3 or 4, regardless of the front or the back of the radiation therapy equipment 1 (see FIG. 3(a) or 4(a)), and also regardless of inward or outward, a total of three combinations is realized when the imaging systems 2 (see the plane view of FIG. 1(a), or FIG. 2) are provided in two sets.

The case will be described where, as opposed to this, the rail 31 for the X-ray tubes 21 and the rail 41 for the X-ray detectors 22 are arranged in the same direction instead of being arranged opposite each other when seen in plane view as shown in FIG. 5.

As shown in FIG. 5, both the rails 31 and 41 describe U-shaped tracks extending around the front of the radiation therapy equipment 1 (see FIG. 5(a)). In FIG. 5, the rail 31 for the X-ray tubes 21 is located inward, and the rail 41 for the X-ray detectors 22 outward. The situation is the same where both the rails 31 and 41 describe U-shaped tracks extending around the back of the radiation therapy equipment 1, and so its description will be omitted. Further, the situation is the same where the rail 31 for the X-ray tubes 21 is located outward, and the rail 41 for the X-ray detectors 22 inward, or where the respective rails 31 and 41 are arranged to overlap each other in plane view, and so its description will be omitted.

As shown in FIG. 5(a), with each having a fixed direction, an arrangement is made such that X-rays emitted from the X-ray tube 21 of one imaging system 2 (see the plane view of FIG. 1(a), or FIG. 2) are detected by the X-ray detector 22 of the same imaging system 2 (see "A" and "a" of FIG. 5(a)). Similarly, an arrangement is made such that X-rays emitted from the X-ray tube 21 of the other imaging system 2 are detected by the X-ray detector 22 of the same imaging system 2 (see "B" and "b" of FIG. 5(a)).

In the case of FIG. 5, as distinct from the case of FIG. 3 or 4, since the rail 31 for the X-ray tubes 21 and the rail 41 for the X-ray detectors 22 are arranged in the same direction instead of being arranged opposite each other when seen in plane view, the respective rails 31 and 41 are open to the same side (in FIG. 5, they are open to the left side of the drawing). Therefore, neither the X-ray tubes 21 nor the X-ray detectors 22 can turn around beyond the open end, and yet the X-ray detector 22 of "b" cannot get ahead of the X-ray detector 22 of "a". For the above reasons, it is impossible to arrange the direction of irradiation of the X-ray tubes 21 and the detecting planes of the X-ray detectors 22 opposite each other as in the modes shown in FIG. 3(c) and FIG. 4(c). And when the X-ray tubes 21 and the X-ray detectors 22 are moved along the rails 31 and 41 (see FIG. 5 (a)) in the directions of arrows in FIG. 5(b), the X-ray detectors 22 will finally detect X-rays emitted from the X-ray tubes 21 in the positions shown in FIG. 5(c).

Thus, the X-ray tubes 21 having fixed directions of irradiation and the X-ray detectors 22 having fixed directions of detecting planes, and when, as shown in FIG. 5, the imaging systems 2 (see the plane view of FIG. 1(a), or FIG. 2) are provided in two sets, realize a combination of directions of X-ray fluoroscopy shown in FIG. 5(a), and a combination of directions of X-ray fluoroscopy shown in FIG. 5(c). Therefore, a total of two combinations are realized, excluding the case of moving the X-ray tubes 21 and X-ray detectors 22 in the same direction.

As described above, in the case where the rail 31 for the X-ray tubes 21 and the rail 41 for the X-ray detectors 22 are arranged in the same direction instead of being arranged opposite each other when seen in plane view as shown in FIG. 5, regardless of the front or the back of the radiation therapy equipment 1 (see FIG. 5(a)), and also regardless of inward or outward, a total of two combinations is realized when the imaging systems 2 (see the plane view of FIG. 1(a), or FIG. 2) are provided in two sets.

Next, the case where the X-ray tubes 21 and X-ray detectors 22 are moved in the same direction will be described with reference to FIG. 6. FIG. 6 presents plane views schematically showing the X-ray tubes and X-ray detectors moved in the same direction along straight tracks of the respective U-shaped tracks.

In FIGS. 6(a) and 6(b), the rail 31 for the X-ray tubes 21 describes a U-shaped track which, as shown in FIG. 3, extends around the front of the radiation therapy equipment 1 (see FIG. 3(a)) and the rail 41 for the X-ray detectors 22 a U-shaped track which extends around the back of the radiation therapy apparatus 1. In FIGS. 6(c) and 6(d), the rail 31 for the X-ray tubes 21 describes a U-shaped track which, as shown in FIG. 4, extends around the back of the radiation therapy equipment 1 (see FIG. 4 (a)) and the rail 41 for the X-ray detectors 22 describes a U-shaped track which extends around the front of the radiation therapy equipment 1.

As shown in FIG. 6(a), with each having a fixed direction, an arrangement is made such that X-rays emitted from the X-ray tube 21 of one imaging system 2 (see the plane view of FIG. 1(a), or FIG. 2) are detected by the X-ray detector 22 of the same imaging system 2 (see "B" and "b" of FIG. 6(a)). Similarly, an arrangement is made such that X-rays emitted from the X-ray tube 21 of the other imaging system 2 are detected by the X-ray detector 22 of the same imaging system 2 (see "A" and "a" of FIG. 6(a)).

On respective straight tracks 31A and 31B (see FIG. 6 (a)) of the U-shaped track of the rail 31 for the X-ray tubes 21 and respective straight tracks 41A and 41B (see FIG. 6(a)) of the U-shaped track of the rail 41 for the X-ray detectors 22, the X-ray tubes 21 and X-ray detectors 22 are moved in the same direction along the tracks 31A, 31B, 41A and 41B. In order to cause movement in the same direction in this way, the sequence control device 7 (see FIG. 2) may control the X-ray tubes 21 and X-ray detectors 22 to move in the same direction while synchronizing them as noted hereinbefore.

FIGS. 6(c) and 6(d) are the same as FIGS. 6(a) and 6(b) except for the front and back of the radiation therapy equipment 1, and therefore their description is omitted. With the movement as shown in FIG. 6, when a gold marker indwelled in a position distant from an isocenter is tracked by X-ray fluoroscopy, for example, the X-ray tubes 21 and X-ray detectors 22 may be moved only by an offset amount in the same direction to the position of the gold marker.

According to the moving object tracking system for radiotherapy in this embodiment having the above construction, by providing two U-shaped track rails for the X-ray tubes 21 and X-ray detectors 22, which include two straight tracks arranged opposite each other and curved tracks connected thereto, X-ray fluoroscopy can be carried out from various directions, as distinct from the simply straight tracks R as shown in the side view of FIG. 9. Compared with the arrangement as shown in the plane view of FIG. 5 in which the U-shaped track rail 31 for the X-ray tubes 21 and the U-shaped track rail 41 for the X-ray detectors 22 are arranged in the same direction instead of being arranged opposite each other when seen in plane view (two combinations in the case of FIG. 5), the arrangement as shown in the plane view of FIG. 3 or 4 in which the U-shaped track rail 31 for the X-ray tubes 21 and the U-shaped track rail 41 for the X-ray detectors 22 are arranged opposite each other can secure an increased number of directions for X-ray fluoroscopy (three combinations in the case of FIG. 3 or 4). As a result, the main problem that the number of sets of the imaging systems 2 consisting of the X-ray tubes 21 and X-ray detectors 22 should be reduced, and X-ray fluoroscopy desirably is carried out from various directions, can be solved. X-ray fluoroscopy can be carried out from various directions when the X-ray tubes 21 and X-ray detectors 22 have fixed directions (directions of irradiation and direction of the detecting planes).

In this embodiment, it is preferable to control the X-ray tubes 21 and X-ray detectors 22 to move in the same direction along the respective straight tracks 31A, 31B, 41A and 41B of the U-shaped track rail 31 for the X-ray tubes 21 and the U-shaped track rail 41 for the X-ray detectors 22. As on the simply straight tracks R as shown in the side view of FIG. 9, on the respective straight tracks 31A, 31B, 41A and 41B of the U-shaped track rail 31 for the X-ray tubes 21 and the U-shaped track rail 41 for the X-ray detectors 22 as shown in the plane view of FIG. 6, the X-ray tubes 21 and X-ray detectors 22 can be moved in the same direction along the tracks 31A, 31B, 41A and 41B. Therefore, movement can be made along the tracks 31A, 31B, 41A and 41B to positions easy to carry out X-ray fluoroscopy. As a result, in addition to the above main problem, a problem that the number of sets of the imaging systems 2 consisting of the X-ray tubes 21 and X-ray detectors 22 should be reduced, and X-ray fluoroscopy desirably is carried out from various positions to enlarge the range of X-ray fluoroscopy, can also be solved when the X-ray tubes 21 and X-ray detectors 22 have fixed directions (directions of irradiation and directions of the detecting planes) on tracks other than the simply straight tracks R as shown in the side view of FIG. 9.

This invention is not limited to the foregoing embodiment, but may be modified as follows:

(1) In the foregoing embodiment, the rail for the X-ray tubes is arranged on the floor, and the rail for the X-ray detectors on the ceiling surface. Conversely, the rail for the X-ray detectors may be arranged on the floor, and the rail for the X-ray tubes on the ceiling surface.

(2) While the foregoing embodiment has been described taking the rails as an example of the U-shaped tracks, the U-shaped tracks may be formed of grooves instead of the rails.

Figure 7:
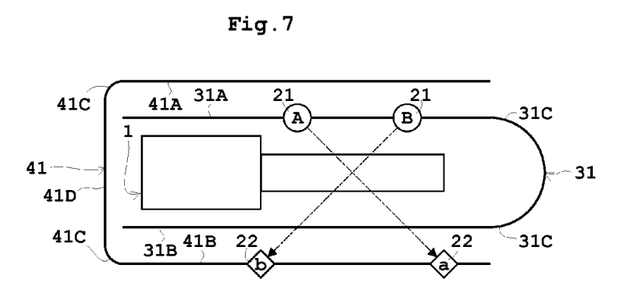
FIG. 7 is a plane view schematically showing a modified example having respective U-shaped tracks arranged opposite each other.

(3) In the foregoing embodiment, in the case of FIG. 3, for example, the rail 31 for the X-ray tubes 21 is a U-shaped track consisting of two straight tracks 31A and 31B arranged opposite each other, curved tracks 31C connected thereto, and a straight track 31D connected to the tracks 31C. As long as it is a U-shaped track consisting of two straight tracks arranged opposite each other and a curved track connected thereto, the U-shaped track may consist only of two straight tracks 31A and 31B and a curved track connected thereto, and not having the track 31D. As shown in FIG. 7, for example, the rail 31 for the X-ray tubes 21 may be formed of a U-shaped track consisting only of two straight tracks 31A and 31B arranged opposite each other and a curved track 31C connected thereto, and the rail 41 for the X-ray detectors 22 may be formed of a U-shaped track which, as in FIG. 3, consists of two straight tracks 41A and 41B arranged opposite each other, curved tracks 41C connected thereto, and a straight track 41D connected to the tracks 41C. The rail 41 for the X-ray detectors 22 located outward, by enlarging the diameter of the curved track, may also be formed of a U-shaped track consisting only of two straight tracks 41A and 41B arranged opposite each other, and curved track 41C connected there.

DESCRIPTION OF REFERENCES

21 . . . X-ray tubes
22 . . . X-ray detectors
31, 41 . . . rails
7 . . . sequence control device

The invention claimed is:

1. A moving object tracking system for radiotherapy for tracking a moving object concerning a treatment part by X-ray fluoroscopy in order to irradiate the treatment part with radiation, comprising:
   an X-ray tube having a fixed direction of X-ray irradiation for the X-ray fluoroscopy;
   an X-ray detecting device with a detecting plane having a fixed direction for detecting X-rays emitted from the X-ray tube to carry out the X-ray fluoroscopy; and
   two U-shaped tracks for the X-ray tube and the X-ray detecting device, each having two straight tracks arranged opposite each other, and a curved track connected thereto;
   wherein the U-shaped track for the X-ray tube and the U-shaped track for the X-ray detecting device are arranged opposite each other when seen in plane view.

2. The moving object tracking system for radiotherapy according to claim 1, comprising a control device for controlling the X-ray tube and the X-ray detecting device to move in the same direction along the straight tracks of the U-shaped track for the X-ray tube and the U-shaped track for the X-ray detecting device, respectively.

* * * * *